(12) United States Patent
Tague et al.

(10) Patent No.: US 6,599,293 B2
(45) Date of Patent: Jul. 29, 2003

(54) DELIVERY DEVICE FOR BONE CEMENT

(75) Inventors: Christopher M. Tague, Portage, MI (US); Dennis A. Stratton, Plainwell, MI (US); James G. Walen, Kalamazoo, MI (US); Richard F. Huyser, Kalamazoo, MI (US)

(73) Assignee: Stryker Instruments, Kalamazoo, MI (US)

( * ) Notice: Subject to any disclaimer, the term of this patent is extended or adjusted under 35 U.S.C. 154(b) by 0 days.

(21) Appl. No.: 09/906,455

(22) Filed: Jul. 16, 2001

(65) Prior Publication Data

US 2003/0014056 A1 Jan. 16, 2003

(51) Int. Cl.[7] .............................. A61B 17/58; A61F 2/00
(52) U.S. Cl. ......................................... 606/94; 222/390
(58) Field of Search ............................. 606/92, 93, 94; 604/211, 224, 232; 222/390, 226

(56) References Cited

U.S. PATENT DOCUMENTS

| | | | |
|---|---|---|---|
| 949,163 A | * 2/1910 | Stapley | |
| 1,612,996 A | 1/1927 | Waagbo | |
| 2,745,575 A | * 5/1956 | Spencer | |
| 2,874,877 A | * 2/1959 | Spencer | |
| 3,144,966 A | 8/1964 | Cook | |
| 3,216,616 A | 11/1965 | Blankenship, Jr. | |
| 3,217,946 A | 11/1965 | Cook | |
| 3,459,341 A | 8/1969 | Copeland | |
| 3,873,008 A | * 3/1975 | Jahn | 222/390 |
| 4,189,065 A | * 2/1980 | Herold | 222/390 |
| 4,269,331 A | * 5/1981 | Watson | 222/390 |
| 4,338,925 A | 7/1982 | Miller | 128/92 |
| 4,371,094 A | 2/1983 | Hutter, III | 222/1 |
| 4,405,249 A | 9/1983 | Scales | 401/182 |
| 4,461,407 A | 7/1984 | Finnegan | 222/391 |
| 4,546,767 A | 10/1985 | Smith | 128/92 |
| 4,583,974 A | * 4/1986 | Kokernak | 604/211 |
| 4,653,487 A | 3/1987 | Maale | 128/92 |
| 4,671,263 A | 6/1987 | Draenert | 128/92 |
| 4,693,656 A | 9/1987 | Guthrie | 411/433 |
| 4,832,692 A | * 5/1989 | Box et al. | 604/211 |
| 4,966,601 A | 10/1990 | Draenert | 606/92 |
| 4,994,065 A | 2/1991 | Gibbs et al. | 606/92 |
| 5,071,040 A | 12/1991 | Laptewicz, Jr. | 222/235 |
| 5,181,636 A | 1/1993 | Anderson et al. | 222/389 |
| 5,306,248 A | * 4/1994 | Barrington | 604/211 |
| 5,308,340 A | * 5/1994 | Harris | 604/211 |
| 5,341,964 A | 8/1994 | Medved | 222/327 |
| 5,431,654 A | 7/1995 | Nic | 606/92 |
| 5,501,374 A | 3/1996 | Laufer et al. | 222/391 |
| 5,514,135 A | 5/1996 | Earle | 606/93 |
| 5,556,009 A | 9/1996 | Motzko | 222/326 |
| 5,638,997 A | 6/1997 | Hawkins et al. | 222/391 |
| 5,681,317 A | 10/1997 | Caldarise | 606/93 |
| 5,762,237 A | 6/1998 | Chang | 222/153 |
| 5,829,875 A | 11/1998 | Hagel et al. | 366/333 |
| 5,893,488 A | 4/1999 | Hoag et al. | 222/391 |
| 6,019,765 A | 2/2000 | Thornhill et al. | 606/94 |
| 6,045,555 A | 4/2000 | Smith et al. | 606/80 |
| 6,048,346 A | 4/2000 | Reiley et al. | 606/92 |
| 6,083,229 A | 7/2000 | Constantz et al. | 606/92 |
| 6,086,594 A | 7/2000 | Brown | 606/92 |
| 6,149,655 A | 11/2000 | Constantz et al. | 606/94 |
| 6,155,463 A | 12/2000 | Dentler | 222/165 |

* cited by examiner

*Primary Examiner*—Ralph A. Lewis
(74) *Attorney, Agent, or Firm*—Howard & Howard

(57) ABSTRACT

A delivery apparatus for injecting cement from a cartridge includes a cradle, a cartridge, a button, and a threaded rod. The cradle has an axial cavity extending therethrough for supporting the cartridge of cement. The cartridge dispensing mechanism is coupled to the cradle. The button includes threads and defines an axial bore. The button is moveable into and out of threaded engagement with the threaded rod. The threaded rod extends into the axial cavity of the cradle.

25 Claims, 5 Drawing Sheets

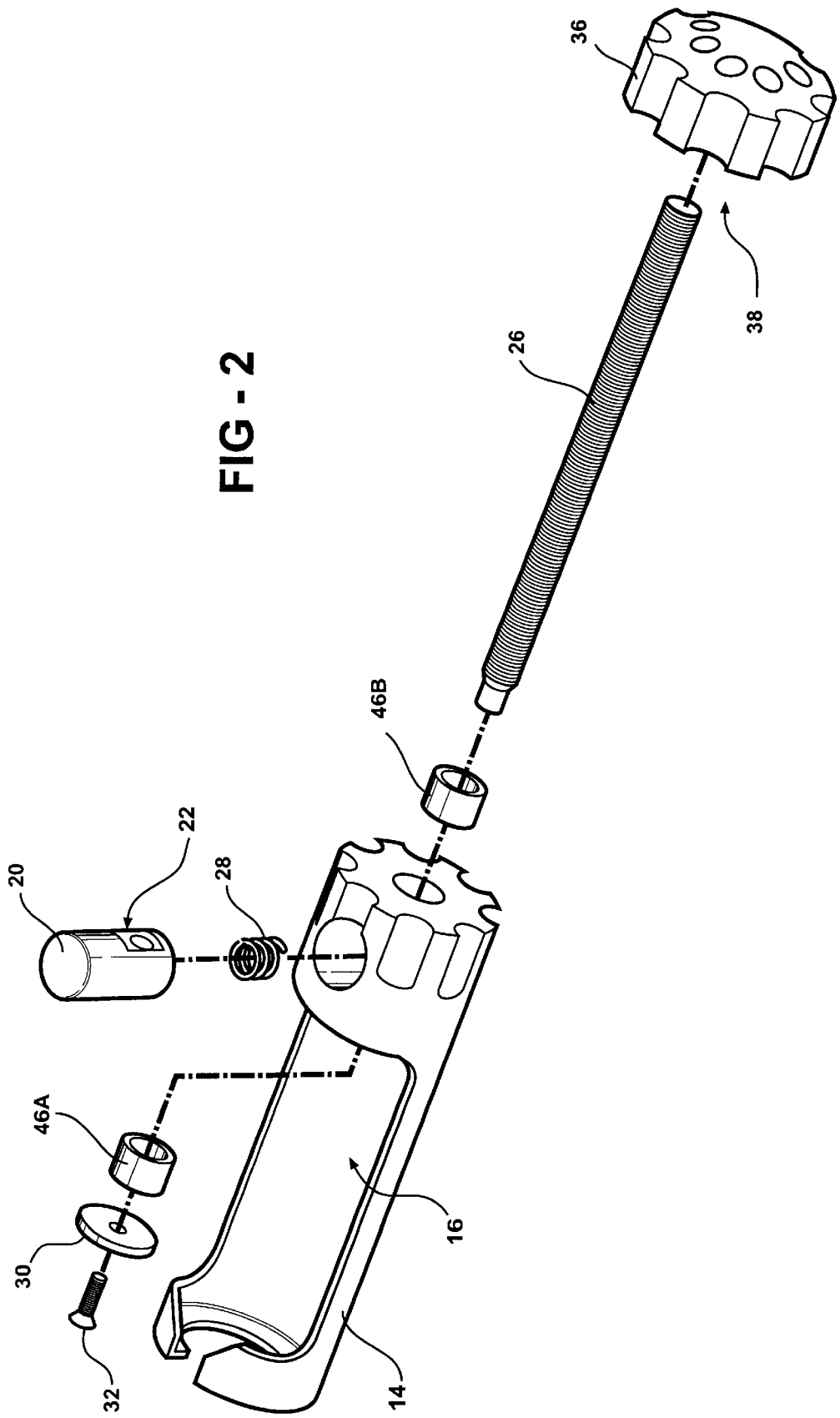

DELIVERY DEVICE FOR BONE CEMENT

FIELD OF THE INVENTION

The invention generally relates to a delivery apparatus for bone cement and, in particular, to a bone cement delivery device that uses a dispensing mechanism for quickly priming the delivery apparatus and delivering the bone cement.

BACKGROUND OF THE INVENTION

The necessity to apply bone cement to a bone during surgical procedures, such as the attachment of a prosthesis or pathological fracture fixation, has been well known in the surgical community. With regard to the attachment of a prosthesis, the cement is packed into the bone and the prosthesis is then attached. The cement cures and a bond develops between the bone and the prosthesis. Traditionally, surgeons have packed the bone cement into the bone by hand. A disadvantage to that technique is that often a weak bond develops between the bone and the prosthesis. When packing the cement by hand the surgeon unknowingly applies insufficient pressure and the cement fails to properly penetrate the bone, thereby creating a weaker bond. Additional disadvantages of packing the cement by hand include excessive time consumption and often the quickly curing cement hardens before the surgeon has finished packing the cement.

Other uses of bone cement include repairing or mending bone fractures or shattered bone occurring from extreme trauma. Bone cement may also be used during cosmetic or dental surgery. Moreover, bone cement may be used as a drug delivery or release system, whereby the bone cement is mixed with antibiotics or other desired drugs and applied to a specific surgical site such that the drugs leach out and are delivered directly to the surgical site. Some bone cements are also designed to be absorbed by the body over time.

To overcome some of these disadvantages, delivery apparatuses have been developed to apply the cement to the bone. One such apparatus greatly resembles a common household caulking gun with a cartridge of caulk. This prior art apparatus has a pistol-shaped body which supports a cartridge of bone cement. The apparatus includes a ram actuated by a movable trigger for pushing the cement out of the cartridge and through a nozzle. A pull of the trigger advances a rod that also advances the ram. The prior art delivery apparatuses also provide structures for adjusting the dispensed quantity of cement per trigger pull. Traditionally this adjustment is accomplished by preventing the full actuation of the trigger with a mechanical stop. The resulting quantity of dispensed cement after the mechanical adjustment is often an imprecise calculation. Additionally, the apparatus delivers a discrete amount of cement per "tooth" of the ram.

The prior art dispensing apparatus have many disadvantages. First, to advance the ram during an initial loading of the cartridge of cement the trigger must be actuated repetitively. This is a very time consuming step during a complex orthopedic surgery. Additionally, a bone cement delivery apparatus must be sterilized prior to being admitted into an operating room. Often the compact design of the delivery apparatus' cartridge dispensing mechanism or trigger assembly makes sterilization in a traditional autoclave unit difficult because the steam is unable to properly penetrate the components of the apparatus.

Currently, there is a need for a delivery apparatus for bone cement with a simple, yet effective design that allows surgeons to quickly prime the apparatus when loading a new cartridge of cement, non-discretely dispensing cement, and properly sterilizing the apparatus.

SUMMARY OF THE INVENTION AND ADVANTAGES

In one embodiment, a delivery apparatus for injecting cement from a cartridge, is provided. The apparatus includes a cradle with an axial cavity extending therethrough for supporting the cartridge of cement. The apparatus also includes a cartridge, a button and a threaded rod. The cartridge dispensing mechanism is coupled to the cradle. The button includes threads and defines an axial bore. The button is moveable into and out of threaded engagement with the threaded rod. The threaded rod extends into the axial cavity of the cradle.

In another aspect of the present invention, a delivery apparatus for injecting cement from a cartridge, is provided. The apparatus includes a cradle with an axial cavity extending therethrough for supporting the cartridge of cement. The apparatus also includes a cartridge dispensing mechanism and a threaded rod. The cartridge dispensing mechanism includes an axial bore and is coupled to the cradle. The threaded rod extends into the axial cavity of the cradle. A first cleaning passageway is defined by the cartridge delivery mechanism and extends from the exterior thereof to the threaded engagement of the rod.

In still another aspect of the present invention, a delivery apparatus for injecting cement from a cartridge, is provided. The apparatus includes a cradle, a cartridge, and a button. The cradle has an axial cavity extending therethrough for supporting the cartridge. The cartridge dispensing mechanism is coupled to the cradle. The button includes threads and defines an axial bore. The button is moveable into and out of threaded engagement. The threaded rod has threads and is in threaded engagement with the axial bore and extends into the axial cavity of the cradle. At least one horizontal base is formed between threads of the button. A top edge of the threads of the threaded rod are in contact with the horizontal base while the button is in threaded engagement with the threaded rod.

Accordingly, it is an object of this invention to provide a quick priming feature for rapidly advancing the threaded rod into contact with the cartridge of bone cement.

It is a further object of this invention is to provide an unrestrictive design of the dispensing mechanism to properly allow steam to penetrate the apparatus through the first cleaning passageway during the sterilization process.

BRIEF DESCRIPTION OF THE DRAWINGS

Other advantages of the present invention will be readily appreciated as the same becomes better understood by reference to the following detailed description when considered in connection with the accompanying drawings wherein:

FIG. 2 is an exploded perspective view of the delivery apparatus of the subject invention;

FIG. 6F is a perspective view of a portion of a button with a wide tooth;

DETAILED DESCRIPTION OF THE PREFERRED EMBODIMENT

Figure 1:
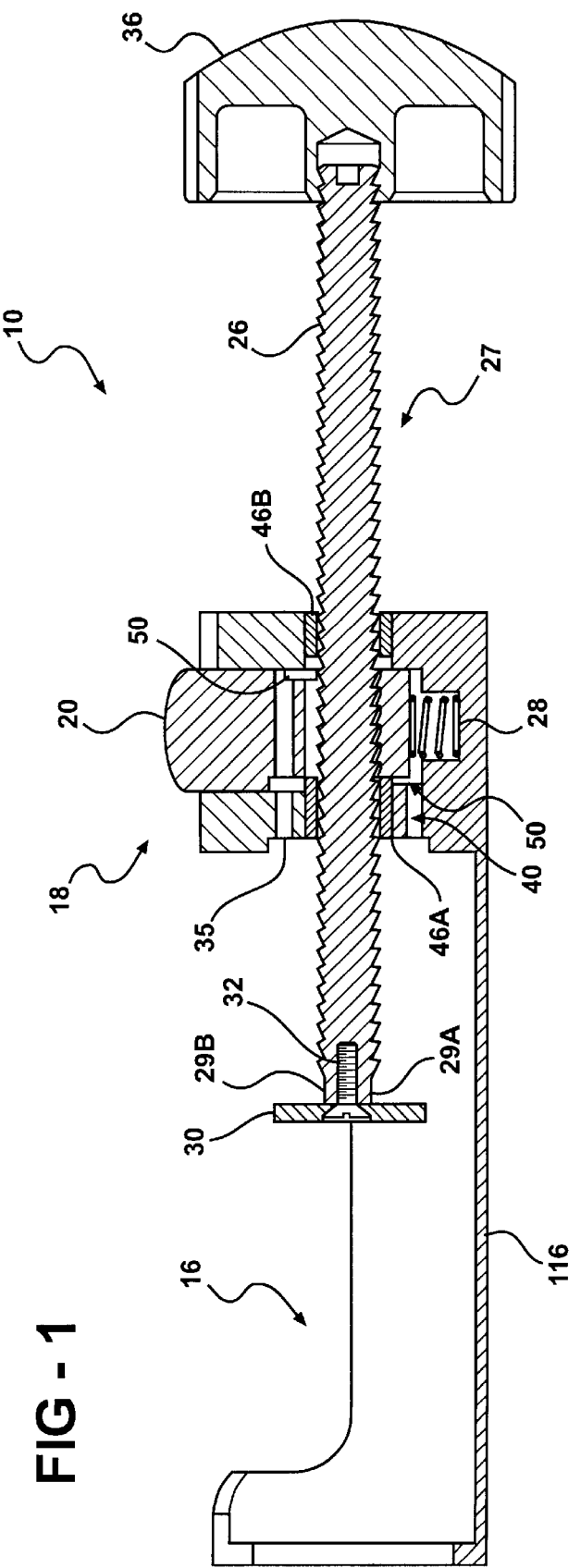
FIG. 1 is a cross-sectional view of a delivery apparatus of the subject invention.

Referring to the Figures, wherein like numerals indicate like or corresponding parts throughout the several views, a delivery apparatus is generally shown at 10 in FIG. 1. The delivery apparatus 10 is used to deliver bone cement from a cartridge 12 to a patient. The cement is applied to bone of the patient to create a bond between the bone and a prosthesis or to fuse a fracture. The delivery apparatus 10 comprises a cradle 14 having an axial cavity 16 extending therethrough. The cradle 14 supports the cartridge 12 of cement in the axial cavity 16. In one embodiment, the cradle 14 is a quick load type cradle, as shown. The quick load cradle 14 includes a semi-open body with a unitarily constructed endcap. In an other embodiment, the cradle is substantially enclosed and has a removable endcap.

In one embodiment, delivery of the bone cement is performed percutaneously. Percutaneous, as used in the medical field, relates to passing or effectuating the bone cement through the skin.

Figure 4A:
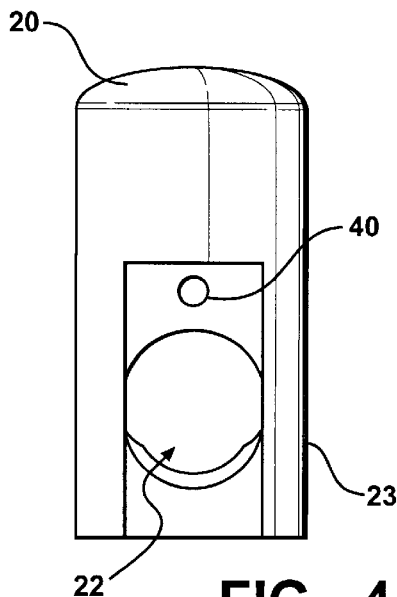
FIG. 4 is an end view of a button of a cartridge dispensing mechanism of the delivery apparatus of FIG. 1.
Figure 4B:
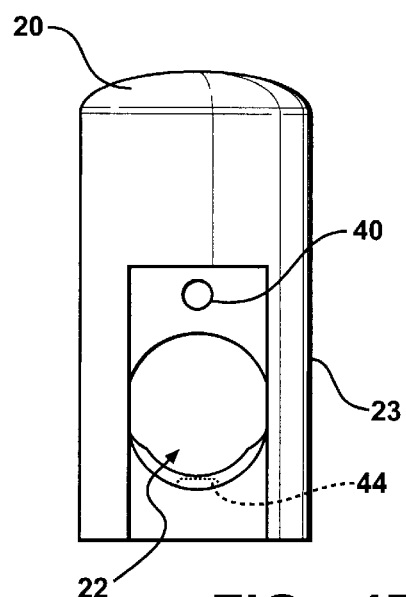
Figure 5:
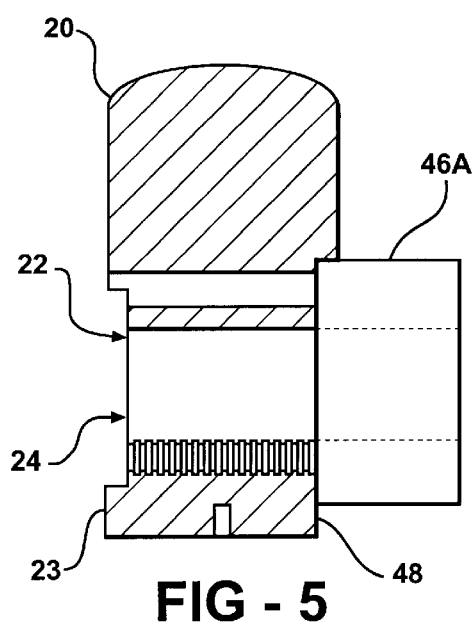
FIG. 5 is a cross-sectional view of the button of the cartridge dispensing mechanism of FIG. 4.

The cradle 14 also supports a cartridge dispensing mechanism generally indicated at 18. The mechanism 18 includes a button 20. In the preferred embodiment, a shown in FIGS. 2, 4 and 5, the button 20 has a generally cylindrical peripheral surface. An axial bore 22 is disposed through and formed by the button 20 and the dispensing mechanism 18. A bottom portion 23 of the axial bore 22 within the button 20 includes threads 24. The threads 24 engage a threaded rod 26 disposed through the axial bore 22. The threaded rod 26 includes a plurality of threads 27. With movement of the button 20, the threads 24 are disengaged from the threads 27 of the threaded rod 26. To permit disengagement, the axial bore 22 has a diameter larger than the diameter of the threaded rod 26.

The threads 24 of the button 20 are moveable into and out of engagement with the rod 26. A biasing device 28 is attached to a terminal end of the button 20. The biasing device 28, in the preferred embodiment, is a compression spring 28. In the absence of an external compressive force, the spring 28 will bias the threads 24 of the axial bore 22 into threaded engagement with the rod 26. To disengage the threads 24 from engagement with the rod 26, an operator must apply a downward compressive force on the top of the button 20. While disengaged, the threaded rod 26 may freely slide through the axial bore 22 to quickly advance the rod 26 into contact with the cartridge 12. This technique is known as priming of the delivery apparatus 10.

One end of the threaded rod 26 includes a disc 30. The disc 30 is attached to the end of the rod 26 with a fastener 32. With the button 20 depressed, the apparatus 10 is primed and the rod 26 and disc 30 are advanced into contact with the cartridge 12. The disc 30 penetrates one end of the cartridge 12 to eject the cement into a nozzle 34. The cement is ejected through the nozzle 34.

For percutaneous delivery, a flexible extension tube (not shown) is removable coupled to the nozzle 34. A needle having a handle (not shown) is coupled to the extension tube for injection through the skin and into the patient. The cement flows through the nozzle 34, extension tube, and needle and into the patient.

Additionally, the cartridge dispensing mechanism 18 includes a recess 35 for receiving the disc 30 when retracted.

The opposite end of the rod 26 includes a handle 36. When the threaded rod 26 is in engagement with the threads 24 of the axial bore 22, the handle 36 is manually rotated to advance the rod 26 and disc 30. This manual rotation dispenses a continuous amount of cement. Advancement of the rod rotationally is used during a surgical procedure to continuously deliver the amount of cement dispensed into the bone of the patient. Preferably, the rod 26 includes first and second flat surfaces 29A, 29B. The flat surfaces are adapted to receive a torque wrench (not shown) to facilitate installation of the handle 36.

Figure 3:
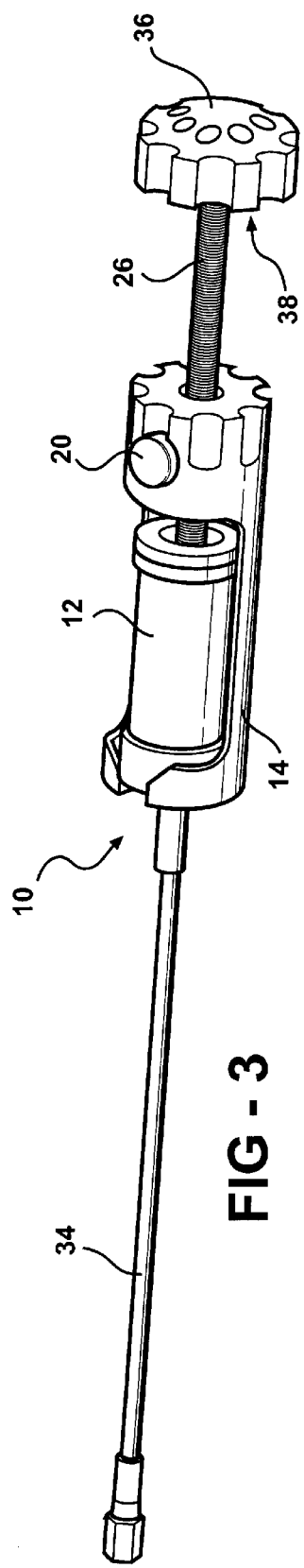
FIG. 3 is a perspective view of the delivery apparatus containing a cartridge of bone cement and includes a nozzle.

In one embodiment, to assist the operator with dispensing a proper amount of cement, the handle 36 includes markings 38. The markings 38 are used to indicate the degree of rotation of the handle 36 and the amount of cement ejected. Rotation of the handle 36 from a first mark to a second mark indicates that the apparatus 10 has ejected a predetermined amount of cement. These markings 38 help guide the operator when using the apparatus 10. For example, as shown in FIGS. 2 and 3, a start position is indicated by an arrow marking on the handle 36. After priming, the arrow may be aligned with a corresponding marking on the cradle by pushing the button 20 down and rotating the handle 36. Thereafter rotation of the handle a portion of its full rotation, e.g., ⅛, delivers a predetermined amount of cement, e.g., 0.2 cc.

Figure 8:
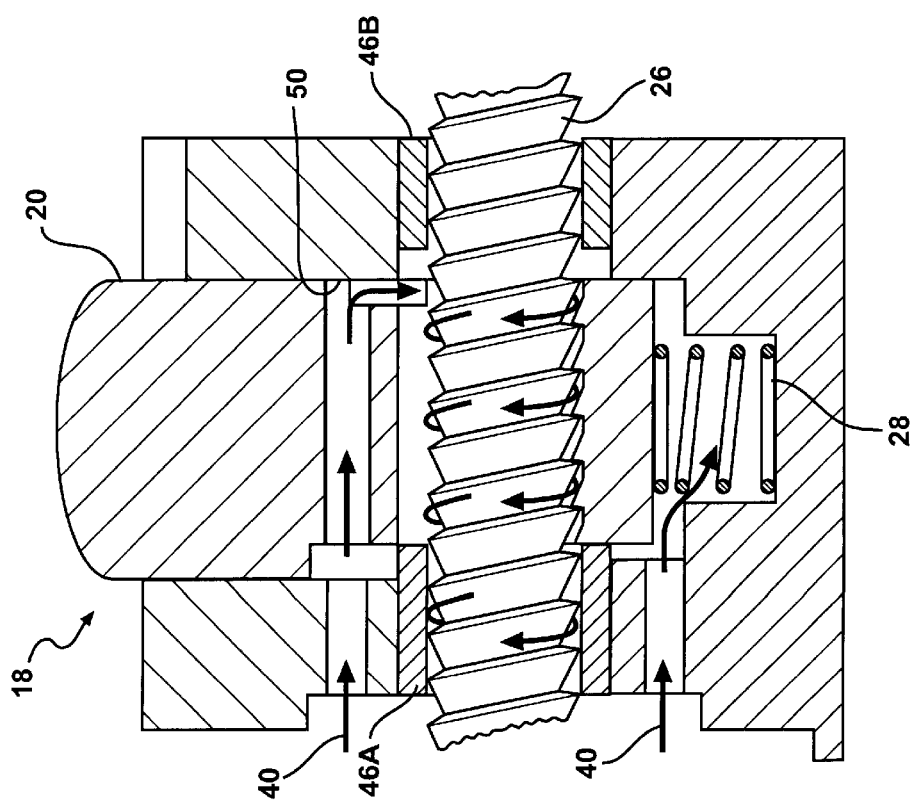
FIG. 8 is a cross-sectional view of the cartridge dispensing mechanism with the threaded rod engaged with the threads of the button.

The cartridge dispensing mechanism 18 defines a first cleaning passageway 40. The passageway 40 extends from the exterior of the mechanism 18 to the threaded engagement of the rod 26. The passageway 40 receives steam during a sterilization process in an autoclave unit. The steam penetrates the mechanism 18 through the passageway 40, as best shown in FIG. 8. The first cleaning passageway 40 assists in ensuring a properly sterilized apparatus 10 suitable for use in an operating room.

The threads 24 of the axial bore 22 of the button 20, while in engagement with the rod 26, also need to receive the steam during sterilization. To accomplish this feat, a second cleaning passageway 42 is created between the threads 24 of the bore 22 and the threaded rod 26. In the preferred embodiment, the threads 24 of the bore 22 are axially spaced from the threaded rod 26 to define the second cleaning passageway 42. The second cleaning passageway 42 allows steam to enter during the sterilization process.

Figure 6B:
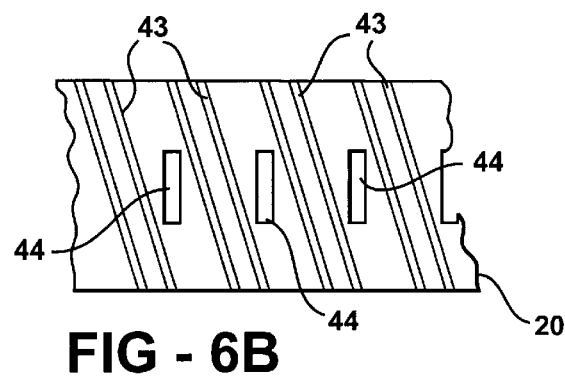
FIG. 6B is a top-down view of the threaded rod of FIG. 6B, according to an embodiment of the present invention.
Figure 6A:
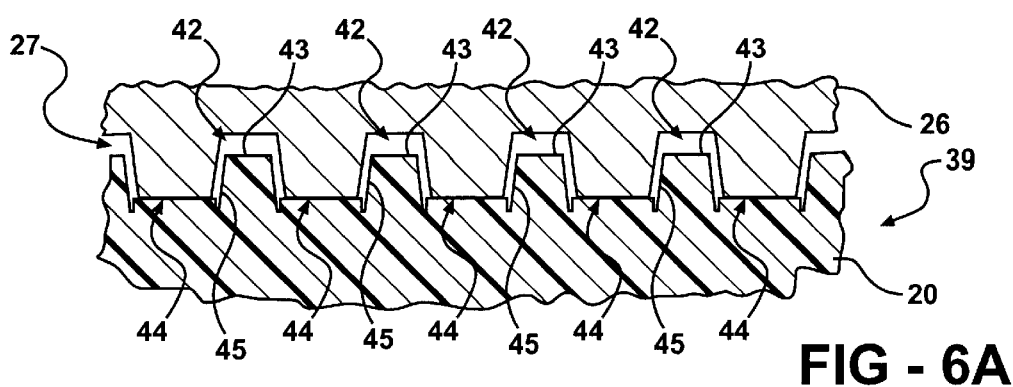
FIG. 6A is an enlarged perspective view of one embodiment of threads of the button of FIG. 4 in engagement with a threaded rod.
Figure 6C:
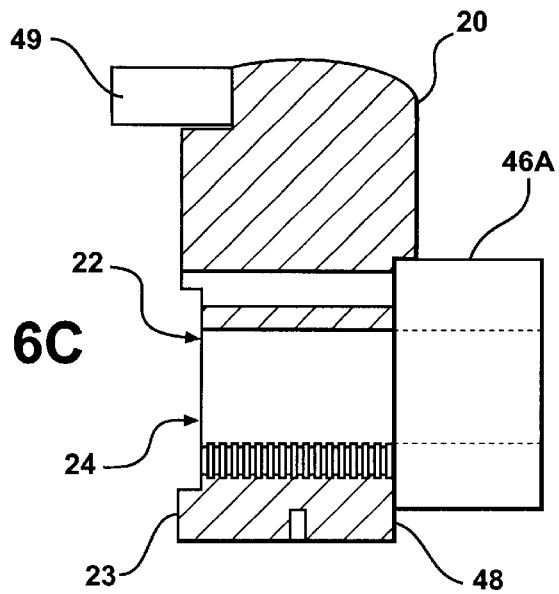
FIG. 6C is a perspective of a portion of the threads of FIG. 6A.

The threads 24 of the axial bore 22 and the rod 26 are axially spaced by a limiting structure 39. In one embodiment, as shown in FIGS. 6A–6C, the limiting structure 39 includes a horizontal base or shelf 44 located in the threads 24 of the axial bore 22. Preferably as shown in FIG. 6B, the horizontal base 44 only extends over a portion of a width of the button 20. Preferably, the threads 43 and the horizontal based 44 are formed simultaneously using an electronic discharge machining process.

The horizontal base 44 prevents the threaded rod 26 from fully penetrating the threads 24 of the axial bore 22. When the button 20 is not being pressed and is therefore biased into engagement with the rod 26, a top edge of the threads 27 of the rod 26 rests along a corresponding horizontal base 44. The horizontal base 44 helps minimize friction or pinching between the threads 24, 27 of the button 20 and the rod 26. As a result, the rotation and advancement of the rod 26 are easier for the operator.

Figure 6D:
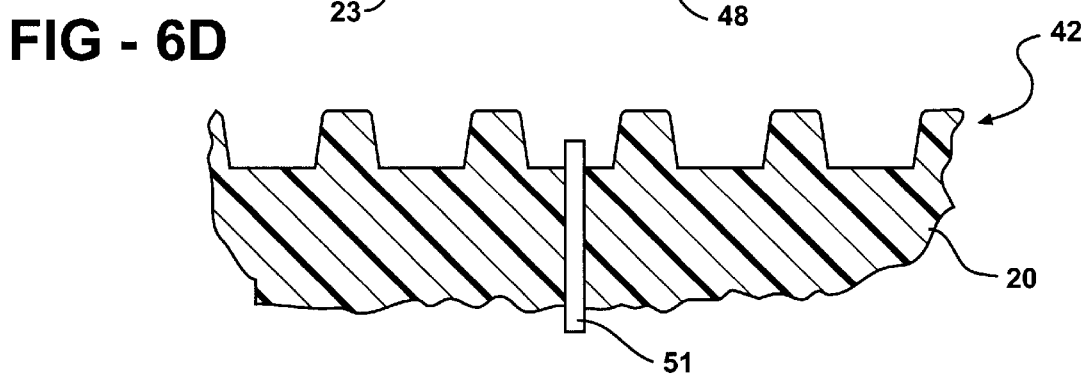
FIG. 6D is a perspective view of a portion of a button with a pin.
Figure 6E:
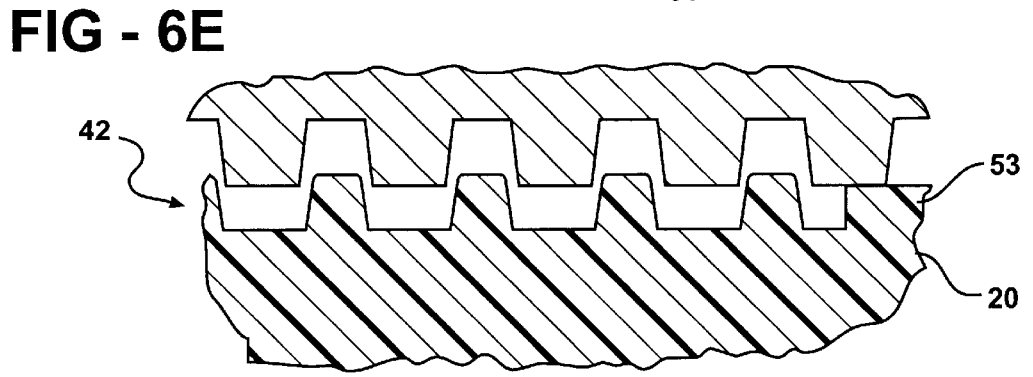
FIG. 6E is a perspective view of a portion of a button with a wide tooth.

In another embodiment as shown in FIG. 6E, the limiting structure 39 includes a stop 49 which limits the travel of the button, thereby minimizing friction and pinching.

In still another embodiment as shown in FIG. 6D, the limiting structure 39 includes one or more pins 51 inserted through the bottom of the button 20 between the threads 24.

In yet still another embodiment as shown in FIG. 6E, the limiting structure 39 includes a wide tooth 53 which engages the threaded rod 26.

Figure 7:
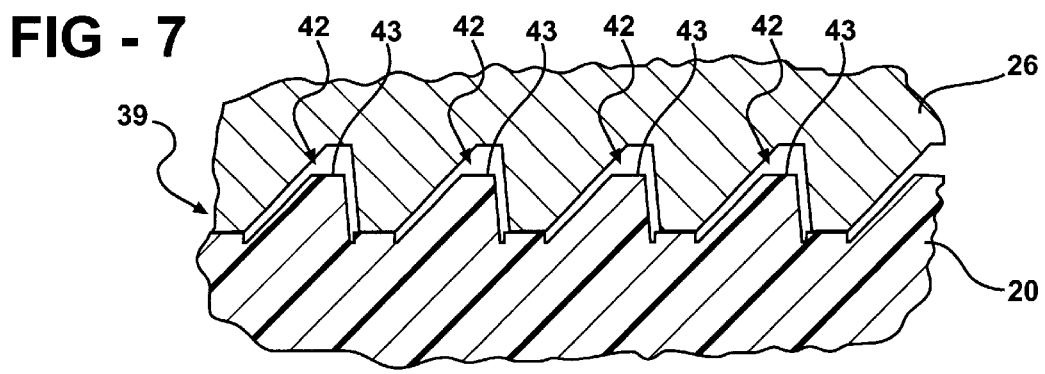
FIG. 7 is an enlarged perspective view of an alternative embodiment of the threads of the button of FIG. 4 in engagement with the threaded rod.

Two alternative threads 24 are shown in FIGS. 6A and 7. Both designs include the limiting structure 39, shown as the horizontal base 44. The threads 24 shown in FIG. 6 show a generally square design with the top 43 of the threads 24 being horizontal. The sides 45 of the threads 24 in FIG. 6 are angled slightly inward, e.g., 5°. Alternatively, the threads 24 shown in FIG. 7 also have a horizontal top 43, but the sides 45 of the threads 24 are angled greatly inward, e.g., 40° or 45° toward the top 43 of the threads 24. The opposite sides are angled slightly, e.g., 7°. The greatly inward angled sides 45 results in the threads 24 in FIG. 7 being generally A-shaped.

Additionally, the threads 24 of the rod 26 and/or the threads of the button 20 may be rounded.

It should be understood that the design of the threads 24, 27 is aimed at reducing the friction in actuating the apparatus and yielding a passageway for receiving steam. As such, modifications may be made to the designs herein described which do not depart from the spirit of the invention.

The cartridge dispensing mechanism 18 also includes first and second bushings 46A, 46B positioned on opposite sides of the button 20 at the axial bore 22. The bushings 46 slidably support the threaded rod 26.

Figure 9:
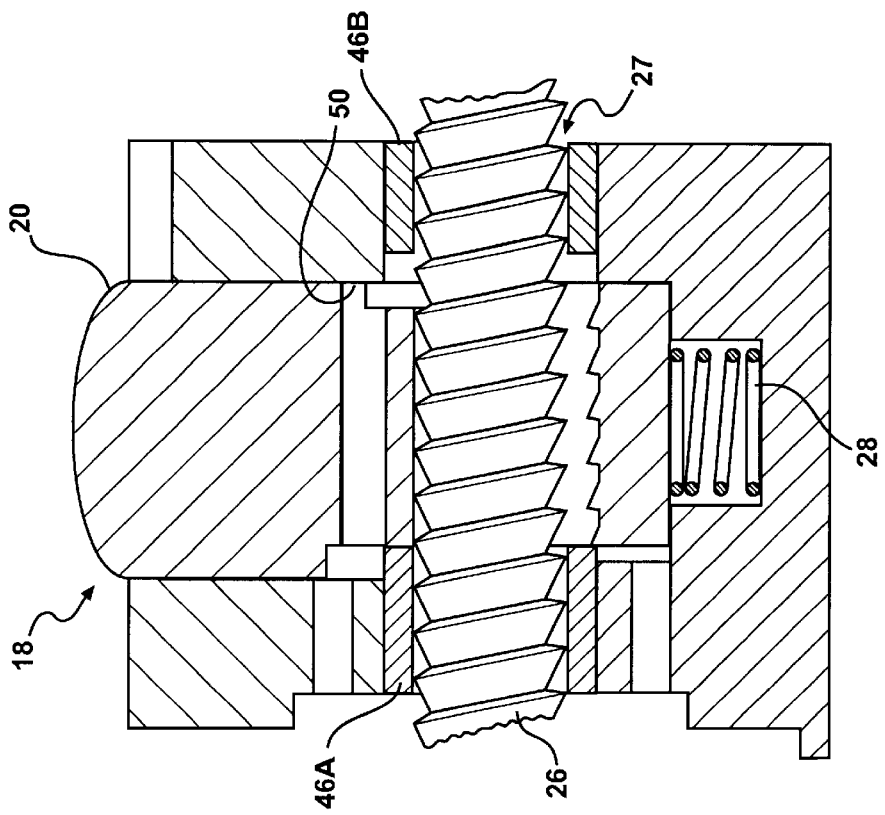
FIG. 9 is a cross-sectional view of the cartridge dispensing mechanism, with the button depressed, showing disengagement of the threaded rod for quickly priming the apparatus.

As shown, in FIGS. 1, 8 and 9, the button 20 includes a recessed flat surface 48. The first bushing 46A extends into the axial bore 22. This allows the button 20 to be inserted into the cartridge dispensing mechanism 18 in only one direction and ensures proper alignment thereof The flat surface 48 engages the first bushing 46A as shown. This arrangement also prevents the button 20 from rotating within the cartridge dispensing mechanism 18 during priming and/or delivery.

The second bushing 46B is located near an interior surface 50 of the cartridge dispensing mechanism 18. The button 20 has a surface which is adjacent the second bushing 46B above and below the rod 26.

Obviously, many modifications and variations of the present invention are possible in light of the above teachings. The invention has been described in an illustrative manner, and it is to be understood that the terminology that has been used is intended to be in the nature of words of description rather than limitation. It will be apparent to those skilled in the art that many modifications and variations of the present invention are possible in light of the above teachings. Therefore, it is to be understood that the invention may be practiced otherwise than as specifically described.

What is claimed is:

1. A delivery apparatus for injecting cement from a cartridge, the apparatus comprising:
    a cradle with an axial cavity extending therethrough for supporting the cartridge;
    a cartridge dispensing mechanism coupled to the cradle;
    a threaded rod extending into the axial cavity of the cradle;
    a button defining an axial bore having threads, the button being moveable into and out of threaded engagement with the threaded rod; and
    at least one base formed between threads of the button, wherein a top edge of the threads of the threaded rod are in contacting with the base while the button is in threaded engagement with the threaded rod.

2. An apparatus, as set forth in claim 1, wherein the mechanism further includes a first cleaning passageway defined by the cartridge delivery mechanism and extending from the exterior thereof to the threaded engagement of the rod.

3. An apparatus, as set forth in claim 1, wherein at least a portion of the threads of the button are spaced from the threaded rod to define a second cleaning passageway for conveying a cleaning medium therethrough.

4. An apparatus, as set forth in claim 1, wherein the axial bore of the button is adapted for moving the button between engaged and disengaged positions.

5. An apparatus, as set forth in claim 4, wherein the axial bore of the button has a diameter greater than a diameter of the threaded rod.

6. An apparatus, as set forth in claim 1, wherein the mechanism further includes a biasing device for biasing the threads of the button into the threaded engagement with the threaded rod.

7. An apparatus, as set forth in claim 1, wherein the mechanism includes bushings slidably supporting the rod.

8. An apparatus, as set forth in claim 7, wherein the button includes a flat surface for engaging one of the bushings to ensure proper alignment of the threads of the button when engaging the threaded rod.

9. An apparatus, as set forth in claim 1, wherein the threaded rod includes a first end and a second end, wherein the apparatus includes a disc attached to the first end of the threaded rod for advancing the ejection of cement from the cartridge.

10. An apparatus, as set forth in claim 9, wherein the mechanism includes a recess for receiving the disc.

11. An apparatus, as set forth in claim 9, including a handle attached to the second end of the threaded rod for manually rotating the threaded rod while in threaded engagement with the threads on the button thereby advancing the disc and ejecting cement from the cartridge.

12. An apparatus, as set forth in claim 11, wherein the handle includes markings for indicating degree of rotation thereof and for indicating the ejection of a predetermined amount of cement from the cartridge.

13. A delivery apparatus for injecting cement from a cartridge, comprising:
    a cradle with an axial cavity extending therethrough for supporting the cartridge;
    a cartridge dispensing mechanism coupled to the cradle;
    a threaded rod having threads and extending into the axial cavity of the cradle;

a button defining an axial bore having threads, the button being moveable into and out of threaded engagement with the threaded rod; and, a limiting structure for limiting a travel of the button and minimizing friction and pinching between the button and the threaded rod, wherein the limiting structure includes at least one horizontal base formed between threads of the button, wherein a top edge of the threads of the threaded rod are in contact with the horizontal base while the button is in threaded engagement with the threaded rod.

14. A delivery apparatus, as set forth in claim 13, wherein the threads of the button are located on a bottom portion of the button.

15. A delivery apparatus, as set forth in claim 14, wherein the horizontal base extends over a portion of a width of the bottom portion of the button.

16. A deliver apparatus, as set forth in claim 13, wherein the limiting structure includes a stop.

17. An apparatus, as set forth in claim 13, wherein the mechanism further includes a biasing device for biasing the threads of the button into the threaded engagement with the threaded rod.

18. An apparatus, as set forth in claim 13, wherein the mechanism includes bushings slidable supporting the rod.

19. An apparatus, as set forth in claim 18, wherein the button includes a flat surface for engaging one of the bushings to ensure proper alignment of the threads of the button when engaging the threaded rod.

20. An apparatus, as set forth in claim 13, wherein the threaded rod includes a first end and a second end, wherein the apparatus includes a disc attached to the first end of the threaded rod for advancing the ejection of cement from the cartridge.

21. An apparatus, as set forth in claim 20, wherein the mechanism includes a recess for receiving the disc.

22. An apparatus, as set forth in claim 20, including a handle attached to the second end of the threaded rod for manually rotating the threaded rod while in threaded engagement with the threads on the button thereby advancing the disc and ejecting cement from the cartridge.

23. An apparatus, as set forth in claim 22, wherein the handle includes markings for indicating degree of rotation thereof and for indicating the ejection of a predetermined amount of cement from the cartridge.

24. A delivery apparatus for injecting cement from a cartridge, comprising;

a cradle with an axial cavity extending therethrough for supporting the cartridge;

a cartridge dispensing mechanism coupled to the cradle;

a threaded rod having threads and extending into the axial cavity of the cradle;

a button defining an axial bore having threads, the button being moveable into and out of threaded engagement with the threaded rod; and, a limiting structure for limiting a travel of the button and minimizing friction and pinching between the button and the threaded rod, wherein the limiting structure includes at least one pin inserted through a bottom of the button between the threads of the button.

25. A delivery apparatus, as set forth in claim 24, wherein the limiting structure includes a wide tooth which engages the threaded rod.

* * * * *